United States Patent [19]

Link et al.

[11] Patent Number: 4,798,914

[45] Date of Patent: Jan. 17, 1989

[54] PROCESS FOR THE PRODUCTION OF VINYL CHLORIDE THROUGH THERMAL CRACKING OF 1,2-DICHLOROETHANE

[75] Inventors: Gerhard Link, Mainz; Walter Fröhlich; Reinhard Krumböck, both of Burgkirchen; Georg Prantl; Iwo Schaffelhofer, both of Burghausen, all of Fed. Rep. of Germany

[73] Assignee: Hoechst Aktiengesellschaft, Fed. Rep. of Germany

[21] Appl. No.: 106,721

[22] Filed: Oct. 8, 1987

[30] Foreign Application Priority Data

Oct. 10, 1986 [DE] Fed. Rep. of Germany ....... 3634550
Feb. 10, 1987 [DE] Fed. Rep. of Germany ....... 3704028

[51] Int. Cl.⁴ .................... C07C 17/34; C07C 21/06
[52] U.S. Cl. .................................. 570/226; 422/200
[58] Field of Search ........................................ 570/226

[56] References Cited

U.S. PATENT DOCUMENTS 3,903,182 9/1975 Rechmeier et al. .

FOREIGN PATENT DOCUMENTS 1127669 7/1982 Canada .

Primary Examiner—Howard T. Mars

[57] ABSTRACT

The hot, vinyl chloride-containing gases leaving the cracking furnace heat liquid 1,2-dichloroethane in a first container to the boiling point or to its immediate vicinity, and the 1,2-dichloroethane is transferred into a second container in which it is partly evaporated under a lower pressure than in the first container. The evaporated 1,2-dichloroethane is fed into the cracking furnace, and the nonevaporated 1,2-dichloroethane is fed back into the first container. By supplying fresh, optionally prewarmed 1,2-dichloroethane into the second container, the amount of product evaporated therein is replaced, the prewarming advantageously being regulated through the level of the liquid 1,2-dichloroethane in the second container. The prewarming of the 1,2-dichloroethane can take place in the convection zone of the cracking furnace or by means of a temperature-control medium, for example steam, which has been heated in the convection zone of the cracking furnace. Compared to processes according to the prior art, higher cracking conversions and a more favorable energy utilization are achieved.

10 Claims, 5 Drawing Sheets

PROCESS FOR THE PRODUCTION OF VINYL CHLORIDE THROUGH THERMAL CRACKING OF 1,2-DICHLOROETHANE

A process for the production of vinyl chloride through thermal cracking 1,2-dichlorethane.

DESCRIPTION

The invention relates to a process as claimed in claim 1 for the production of vinyl chloride, and to an apparatus as claimed in claim 14 for carrying out the process.

Incomplete thermal cracking of 1,2-dichloroethane at pressures from 1 to 4 MPa and temperatures from 450° to 550° C. for the production of vinyl chloride has been carried out for many years on a large industrial scale. One problem in this process is the by-products which are formed at the high temperatures and which can lead, inter alia, to formation of coke and blockages in the pipes of the pyrolysis furnace. It is therefore usual to remove these by-products by distillation from the unreacted 1,2-dichloroethane before it is recycled into the process. However, undesired by-products again form in this purified 1,2-dichloroethane during heating and, particularly, during evaporation before cracking; these by-products can lead to problems during cracking caused by baking-on to the cracking tubes.

For partial removal of these by-products, it is known from Canadian Pat. No. 1,127,669 to partially evaporate 1,2-dichloroethane in the upper part of the pyrolysis furnace at a temperature from 200° to 250° C. and a pressure from 20 to 35 atm (about 2 to 3.5 MPa), to remove, in a separator, the liquid part of the mixture of vaporous and liquid 1,2-dichloroethane, and, after filtration, if appropriate with admixing of fresh 1,2-dichloroethane, to feed it back into the upper part of the pyrolysis furnace while the 1,2-dichloroethane vapors escaping via the head of the separator are passed into the lower part of the pyrolysis furnace and cracked there. The partial evaporation of the 1,2-dichloroethane can take place in an apparatus which is heated separately from the pyrolysis furnace using fuel. A pump is used to transport the liquid 1,2-dichloroethane.

The pump and filters make the apparatus for this process expensive and susceptible to faults. It permits utilization of the heat contained only in the exhaust gases from the pyrolysis furnace, but not the heat contained in the cracking product gases. It cleans the heated 1,2-dichloroethane only from solid (coke) particles, but not from likewise undesired, liquid contaminants which, according to experience, form coke during subsequent cracking. In practice, maximum cracking conversion of 54% is achieved.

In order to use the heat which is contained in the vinyl chloride-containing cracking product gases, it is known from Canadian Pat. No. 1,127,669 to cool these gases in a heat exchanger through which liquid 1,2-dichloroethane flows as coolant through the jacket side. This 1,2-dichloroethane is fed to the cracking zone in gas form after heat take-up. Purification of the 1,2-dichloroethane during or after warming is not provided, and a higher conversion than by the process of U.S. Pat. No. 3,903,182 cannot be achieved. A further disadvantage is the rigid coupling of the energy-providing cracking product gas to the 1,2-dichloroethane stream to be warmed, it not being possible to compensate for variations which always occur during production.

A process has now been found which makes it possible to utilize the heat contained in the cracking product gases, to clean the warmed 1,2-dichloroethane from solid and relatively high-boiling, liquid contaminants and to compensate for production variations in a flexible manner, a relatively high cracking conversion being achieved at a comparable run time than is the case using the process according to the prior art.

The novel process for the preparation of vinyl chloride through thermal elimination of hydrogen chloride from 1,2-dichloroethane in a cracking furnace, liquid 1,2-dichloroethane being indirectly warmed and evaporated using the hot, vinyl chloride-containing gas leaving the cracking furnace, and the gaseous 1,2-dichloroethane being introduced into the cracking furnace, comprises warming the 1,2-dichloroethane to boiling in a first container with the vinyl chloride-containing gas, and transferring it from there into a second container in which it is partially evaporated without further warming under a lower pressure than in the first container, the evaporated 1,2-dichloroethane being fed into the cracking furnace and the nonevaporated 1,2-dichloroethane being fed back to the first container.

The evaporated 1,2-dichloroethane is replaced by feeding in fresh, liquid 1,2-dihloroethane, the level of the liquid 1,2-dichloroethane in the second container advantageously being maintained so that a large liquid surface area is available. In a preferred embodiment of the novel process, the fresh, liquid 1,2-dichloroethane is fed into the second container, the temperature previously being regualted using temperature-control agents, such as, for example, water, steam, liquids which contain 1,2-dichloroethane and which are employed again at another point of the process, or oil. In this embodiment, the level of the liquid in the second container is expediently used as the regulating variable.

The amount of the evaporated 1,2-dichloroethane can vary within broad limits. Advantageously, 1,000 to 10,000 kg of 1,2-dichloroethane per hour and, in particular, 2,000 to 5.000 kg of 1,2-dichloroethane per hour are evaporated per square meter of surface area of the liquid taken as resting in the second container. The surface area of the liquid taken as resting can easily be determined from the dimensions of the second container, taking into account the level of the liquid. In fact, the surface is in constant motion while the process is being carried out, through which it is somewhat larger than the surface taken as resting. However, it is extremely difficult to determine the rapidly changing, actual surface area, if not even impossible.

The temperature at which the fresh, liquid 1,2-dichloroethane is fed to the two containers which are used for evaporation can vary within broad limits, the lower limit being determined by the heat contained in the cracking product gases and it being possible for the upper limit to be a few degrees below the temperature at which 1,2-dichloroethane evaporates from the second container. The 1,2-dichloroethane used for the process according to the invention is expediently already prewarmed. The fresh, liquid 1,2-dichloroethane is advantageously fed to the second container at a temperature from 150° to 220° C., in particular from 170° to 210° C., this temperature being selected so that it is at least 20° C. below the temperature at which 1,2-dichloroethane in gas form leaves the second container. The pressure of 1,2-dichloroethane during prewarming until introduction into the second container should be sufficiently high to prevent premature boiling of the fed liquid.

Various methods are suitable for prewarming the liquid, fresh 1,2-dichloroethane, for example it can take place by means of steam, heated, high-boiling liquids, for example mineral oil or molten diphenyl, using the hot combustion gases of the burner installed especially for this purpose, or through electrical heating. In a preferred embodiment of the novel process, the fresh, liquid 1,2-dichloroethane is warmed, before it is fed into the second container, in the convection zone of the cracking furnace using the exhaust gas which the burners heating the cracking furnace produce. In a further preferred embodiment of the novel process, the fresh, liquid 1,2-dichloroethane is warmed using a heating medium which is itself warmed in the convection zone of the cracking furnace using the exhaust gas which the burners heating the cracking furnace produce. Suitable heating media for this are, as already stated, heated, high-boiling liquids, such as mineral oil, silicone oil or molten diphenyl, and also, in particular, steam.

The 1,2-dichloroethane is warmed indirectly to boiling in a first container with vinyl chloride-containing gas. A heat exchanger is expediently utilized for this purpose, the hot vinyl chloride-containing gas flowing from the cracking furnace through at least one pipe, which can be essentially straight or can be bent in a helical, spiral or meander shape. This pipe is surrounded by the liquid 1,2-dichloroethane to be warmed. It is advantageous when, during the indirect warming of the 1,2-dichloroethane in the first container, the hot, vinyl chloride-containing gas from the cracking furnace is cooled at an average cooling rate, per second, of at least 1/15 of the temperature in degrees Celsius, at which this gas enters the indirect warming zone for the 1,2-dichloroethane, until a temperature is reached which is at least 5° C. above the evaporation temperature of the 1,2-dichloroethane in the second container. If, for example, the hot vinyl chloride-containing gas enters the first container at a temperature of 525° C., the average cooling rate should be at least 525/15=35° C. per second. If the 1,2-dichloroethane in the second container evaporates, for example, at 260° C., the temperature of the vinyl chloride-containing gas on leaving the first container should be at least 265° C. The cooling rate of the vinyl chloride-containing gas in the first container can be very high. At, per second, more than 1/5 of the temperature, in degrees Celsius, at which this gas enters the indirect warming zone for the 1,2-dichloroethane, it generally becomes industrially more and more difficult to achieve the heat transfer necessary for such high cooling rates. The upper limit for the temperature at which the vinyl chloride-containing gas leaves the indirect warming zone for the 1,2-dichloroethane is, of course, determined by the entry temperature of the vinyl chloride-containing gas into this zone, but, for economic reasons, it is generally not more than 50° C. above the evaporation temperature of the 1,2-dichloroethane in the second container.

In the first container, the 1,2-dichloroethane is warmed to boiling. The 1,2-dichloroethane thus warmed is transferred into a second container in which it is partially evaporated, without further warming, under a lower pressure than in the first container. This flow of the liquid, warmed 1,2-dichloroethane from the first container into the second and also the flow of the non-evaporated 1,2-dichloroethane from the second container back into the first advantageously takes place without the use of mechanical transport means, but instead through so-called "natural circulation". This is caused by the 1,2-dichloroethane at the boiling point rising in at least one pipe from the first container into the second container located above the former, driven by the effect that the liquid 1,2-dichloroethane, initially containing relatively few vapor bubbles, has a specific gravity less than that of the liquid containing no vapor bubbles, which causes it to collect at the top of the first container and to leave through a pipe leading upwards. On the way upwards, the pressure decreases, causing more and more 1,2-dichloroethane to evaporate. This leads to the volume of the liquid/vapor mixture constantly increasing and the specific gravity of this mixture decreasing. Finally, the liquid/vapor mixture reaches the second, upper container, in which it separates into the two phases. The vapor phase is drawn off in the upper part of the second container and fed into the cracking zone of the pyrolysis furnace. The nonevaporated, liquid 1,2-dichloroethane collects in the lower part of the second, upper container, from which it is fed back through at least one pipe into the lower part of the first container. The liquid which contains no vapor bubbles and which is cooler, and thus has a greater specific gravity, due to supply of cooler, fresh 1,2-dichloroethane into the second, upper container flows in this pipe back into the first, lower container. Here, it is warmed to boiling by the hot, vinyl chloride-containing gas, and the cycle starts anew. The amount of 1,2-dichloroethane circulated ($m_u$) can be calculated according to the following formula from the amount of fresh 1,2-dichloroethane supplied ($m_o$), its temperature ($t_o$) and the temperature ($t_1$) of the liquid flowing in the pipe from the second, upper container into the first, lower container and the temperature ($t_2$) of the liquid rising from the first container into the second:

$$m_u = \frac{m_o \cdot (t_1 - t_o)}{(t_2 - t_1)}$$

The amount of fresh 1,2-dichloroethane fed into the second container, relative to 100 kg of the 1,2-dichloroethane circulating per hour between the first and second containers, can vary within broad limits, 2 to 20 kg, and in particular 3 to 10 kg, of fresh 1,2-dichloroethane, relative to 100 kg of 1,2-dichloroethane circulating per hour, are advantageously fed into the second container.

In a preferred embodiment of the process according to the invention, part of the liquid 1,2-dichloroethane from the first container, in which it is warmed to boiling, is drawn off, if necessary separated from solid components, and fed into a distillation column. A distillation column in which 1,2-dichloroethane is distilled off overhead, and which is present anyway in order to purify thermally uncracked 1,2-dichloroethane before reuse, is advantageously used for this purpose. In this case, only the coarser solid components need be removed, if any at all, which can be accomplished, for example, using a simple sieve. It has proven particularly favorable to draw off from the first container 0.5 to 7 kg of liquid 1,2-dichloroethane per hour per 100 kg per hour of the liquid 1,2-dichloroethane freshly fed into the second container.

The temperature at which the 1,2-dichloroethane evaporated in the second container leaves this container can vary within broad limits. This temperature is advantageously 170° to 280° C., in particular 220° to 280° C. This temperature is expediently adjusted by regulating the pressure at the head of a column for removing hydrogen chloride from the vinyl chloride-containing gas which leaves the first container after indirect heat exchange, the head temperature of this column being −20° to −50° C.

The average residence time of the 1,2-dichloroethane in the first and second containers together should not be too long, in particular at relatively high evaporation temperatures of the 1,2-dichloroethane, since this favors formation of by-products. The process is advantageously carried out at average residence times from 15 to 90 minutes, but longer residence times are also possible, above all at lower evaporation temperatures, but are often also not desirable for economic reasons. In order to achieve the maximum cracking conversions while keeping the composition of the cracking products constant, it is desirable to feed the 1,2-dichloroethane evaporated in the second container into the cracking furnace at the most constant rate per hour possible. This can be achieved particularly well using the novel process as a consequence of its favorable regulation possibilities.

The temperature of the pipes in the cracking furnace in which the 1,2-dichloroethane is cracked into vinyl chloride and hydrogen chloride is expediently adjusted by regulating the fuel feed to this furnace, so that 60 to 70% by weight of the 1,2-dichloroethane evaporated according to the invention which is fed into this furnace are thermally cracked. It is favorable here to heat the cracking furnace conventionally used with several rows of burners arranged above one another, in a fashion such that 1 to 2.3 kg of fuel are fed to the upper rows of burners for each kilogram of fuel which is fed to the lower rows of burners. However, a different type of heating of the cracking furnace is also possible.

The 1,2-dichloroethane evaporated in the first container can be fed either to the radiation zone or to the convection zone of a conventional cracking furnace, "radiation zone" designating the part of the furnace in which the 1,2-dichloroethane transported in at least one pipe is subjected to the direct radiation heat of the burner flames which heat the furnace, whereas "convection zone" designates the part of the furnace in which the 1,2-dichloroethane transported in at least one pipe is essentially warmed only by the hot exhaust gases which the burners produce. The evaporated 1,2-dichloroethane is advantageously fed into the cracking furnace at the beginning of the radiation zone.

However, it may also be advantageous in certain cases, depending on the furnace design and the heating, to move the feed point to the part of the convection zone which is adjacent to the radiation zone and to use the remaining part of the convection zone, for example, for prewarming the liquid 1,2-dichloroethane before evaporation.

Figure 1:
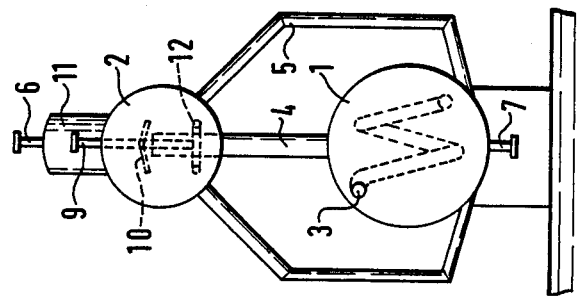
FIGS. 1-5 illustrate apparatus for the production of vinyl chloride according to the invention described herein.
Figure 1:
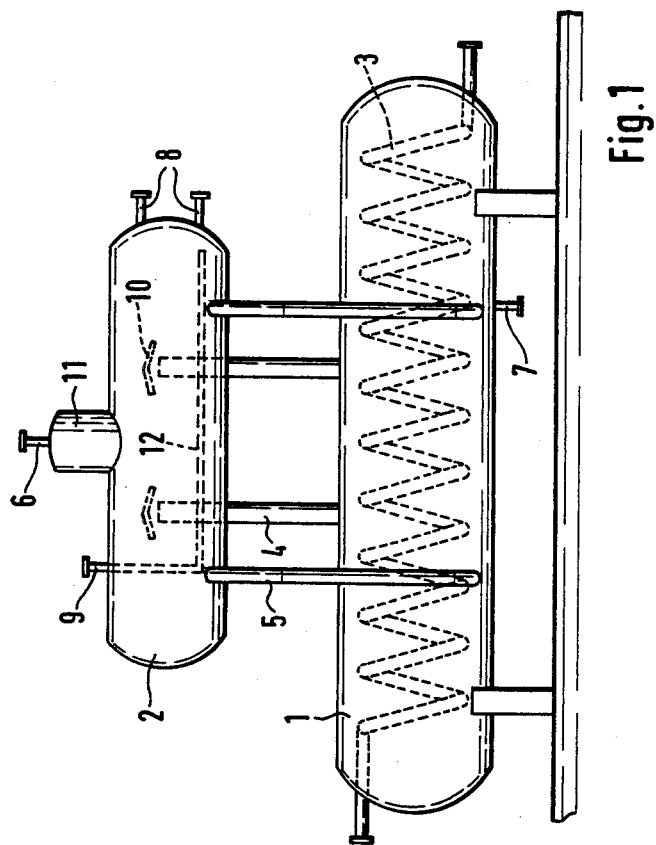

The invention also relates to an apparatus for carrying out the process described above; an example of such an apparatus is represented in FIG. 1. The various parts of the apparatus are labeled in this figure with numbers to which the numbers shown in parentheses below relate. The apparatus comprises two closed, cylindrical containers (1; 2) whose length to diameter ratio is 2 to 8 which are connected to one another through pipes and of which one container contains a coiled pipe (3), and wherein the two containers (1; 2) are arranged substantially parallel above one another at a distance with a cylinder axis which is horizontal or slightly inclined to the horizontal, the lower container (1) contains the coiled pipe (3), at least one rising pipe (4) leads from the uppermost part of the lower container (1) into the upper container (2) and ends open in the upper half of the latter, at least one connecting pipe (5) leads from the lower part of the upper container (2) to the lower part of the lower container (1), the lower container (1), in the lower part, and the upper container (2), in the upper part, each contain an aperture (6; 7), and the upper container (2) has a liquidlevel measurement device (8) and at least one further aperture (9) from which a pipe leads into the lower part of this container. The two cylindrical containers are arranged with horizontal cylinder axes in order to give a greater liquid surface area compared to a container having a vertical cylinder axis. For the same reason, the length to diameter ratio in both vessels should not be substantially below 2. The process according to the invention can also be carried out in very slim containers having a high length: diameter ratio, but economic and design misgivings are against selecting a ratio which is too high. In general, 8 will not be exceeded. The upper container (2) need not necessarily be arranged precisely vertically above the lower container (1), neither is it necessary for the upper container (2) to be smaller than the lower. The upper container expediently contains a dome (11) into which the aperture (6) is introduced. The rising pipes (4) and the connecting pipes (5) should be arranged so as to be approximately uniformly distributed over the length of both containers, a larger cross-section favorably being selected for the rising pipes (4) than for the connecting pipes (5). The number and cross-section of both pipe types depend on the length of the containers (1; 2) and on the amount of liquid 1,2-dichloroethane circulating in the two containers, the calculation for which is described above. Furthermore, it is not absolutely necessary to arrange the connecting pipes (5) opposite each other in pairs.

The upper end of the rising pipe or the rising pipes (4) is advantageously covered with a hood (10) so that an annular aperture remains free between this hood and the end of the pipe. This causes the separation of the liquid phase from the gaseous phase in the upper container (2) to be improved.

The upper container (2) can have one or more apertures (9) from which pipes lead into the lower part of this container. In a preferred embodiment of the apparatus according to the invention, only one such aperture is used from which a pipe leads into the lower part of the container, a horizontal pipe loop (12) which is closed at the end and which contains apertures distributed uniformly along its length being attached to the end of this pipe.

As stated above, the novel process makes it possible to reuse the heat contained in the vinyl chloride-containing gases leaving the cracking furnace and thus to save energy. The process can be carried out in an apparatus which contains no parts which are susceptible to faults (pump and filters for hot 1,2-dichloroethane). Through favorable regulation possibilities, the novel process can be matched flexibly to production variations, and, at a comparable cracking furnace run time, a markedly higher cracking conversion can be produced than using corresponding processes according to the prior art.

The following examples are intended to illustrate the invention in greater detail, but it is not limited to these examples.

Figure 2:
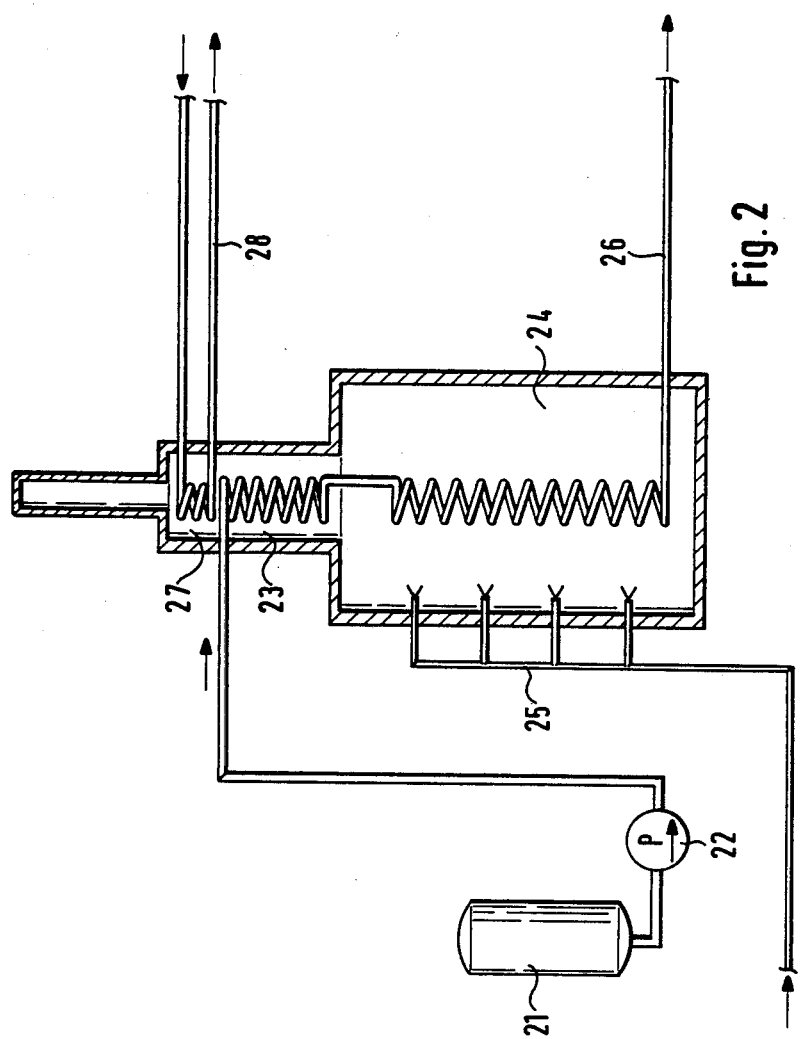

For comparison, a process is initially used which is also used on a large industrial scale for the preparation of vinyl chloride by thermal cracking of 1,2-dichloroethane; in this respect, see the flowchart represented in FIG. 2.

902 kg of 1,2-dichloroethane having a temperature of 130° C. are drawn off per hour from a pump reservoir (21) and transported by means of the pump (22) under a pressure of 3.0 MPa and at a temperature of 125° C. into the convection zone (23) of the cracking furnace (23 plus 24).

In this zone, 1,2-dichloroethane is heated to the boiling point, evaporated and transported further, with a temperature of 270° C., into the radiation zone (24) of the cracking furnace (23 plus 24). The superheating and partial cracking of the gaseous dichloroethane to form vinyl choride and hydrogen chloride takes place in the radiation zone (24) to a temperature of 533° C. The radiation zone (24) contains four rows of burners (25) arranged one above the other, of which, however, only the three lower rows are fed with fuel. In order to reduce the formation of soot during evaporation of 1,2-dichloroethane, the fourth, uppermost row of burners is not used.

The hot cracking product gases leaving the cracking furnace through the pipe (26) are cooled in the subsequent cooling stage to a temperature of less than 100° C. under a pressure of 1.6 MPa. After further cooling stages, the removal of hydrogen chloride from the mixture produced through thermal cracking takes place in a column which is operated under a pressure of 1.3 MPa and a head temperature of −24° C.

The exhaust gas cools to about 350° C. through the heat exchange in the convection zone (23) between the exhaust gas which is passed around the pipes and the 1,2-dichloroethane in the pipes. Further cooling of the exhaust gas to about 150° C. takes place in an economizer (27) through production of hot water. In this economizer, 480 dm$^3$ of kettle feedwater per hour can be warmed from 80° C. to 150° C. under a pressure of 2.5 MPa. The warmed kettle feedwater is fed to the steam generation stage via the pipe (28). This steam is used elsewhere in the vinyl chloride production process.

312.5 kg of vinyl chloride per hour are produced, the cracking conversion being 55% and the cracking furnace run time being a maximum of 6 months. 0.115 Nm$^3$ of fuel (methane) are used per kg of vinyl chloride produced. The energy recovered from the exhaust gases through production of hot water is 448.2 kJ/kg of vinyl chloride, corresponding to 0.0126 Nm$^3$ of fuel per kg of vinyl chloride. The effective fuel consumption is thus reduced to 0.1024 Nm$^3$/kg of vinyl chloride.

The 1,2-dichloroethane used has a purity of 99.731% by weight, the remainder being by-products. For this comparison experiment and for the following examples, a 1,2-dichloroethane of the same purity and having the same type and quantity of by-products is used.

EXAMPLE 1

Figure 3:
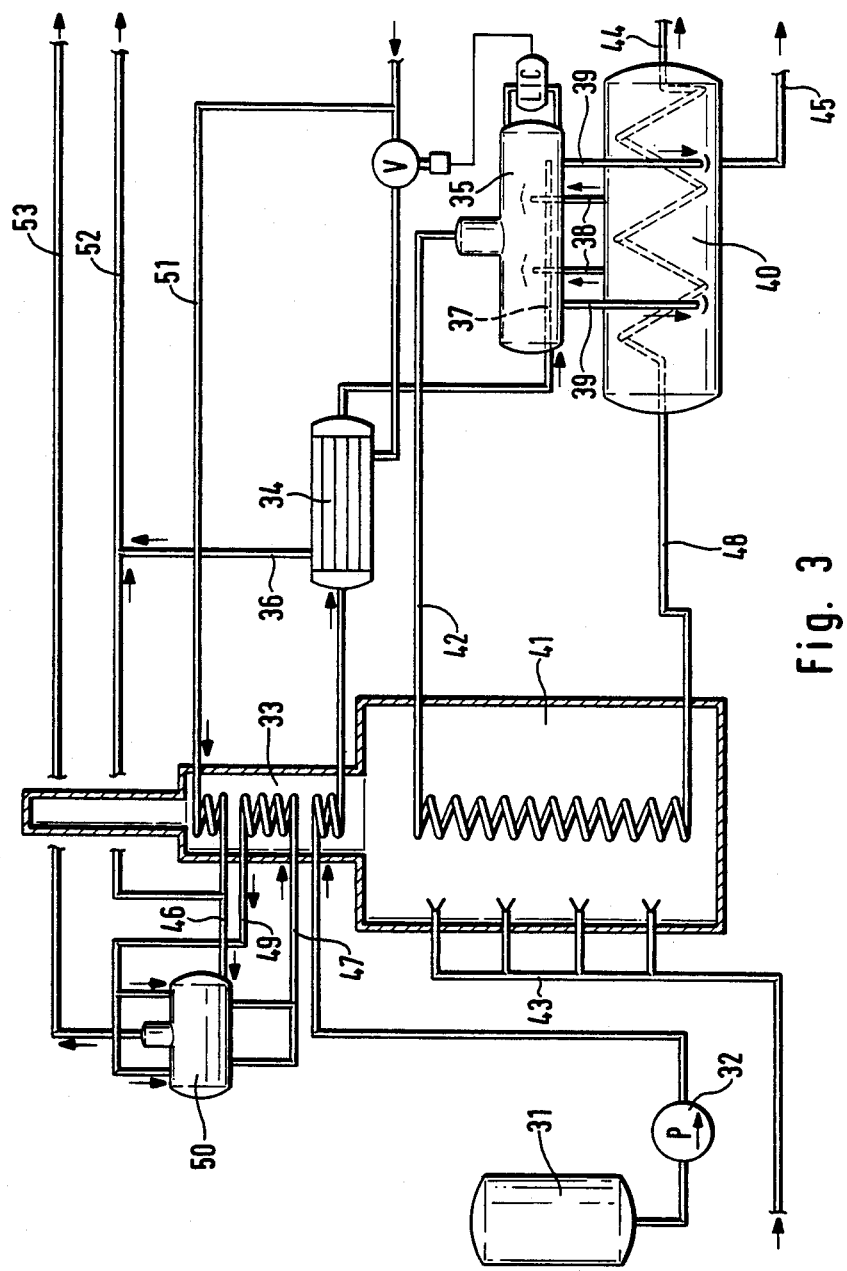

A procedure is followed as shown in the flowchart represented in FIG. 3. From a pump reservoir (31), 834 kg of 1,2-dichloroethane having a temperature of 130° C. are drawn off per hour and transported by means of the pump (32) under a pressure of 4.0 MPa and at a temperature of 125° C. into the lower part of the convection zone (33) of the cracking furnace (33 plus 41). The liquid 1,2-dichloroethane is warmed to 220° C. by the exhaust gases drawn off from the radiation zone (41) of the cracking furnace, the exhaust gases being cooled from 930° C. to 710° C. The energy equalization between the region (33) providing energy for the liquid 1,2-dichloroethane, and the take-up of energy in the first container (40) required for evaporation of the 1,2-dichloroethane takes place in the heat exchanger (34). For this purpose, the level of the liquid 1,2-dichloroethane in the second container (35) is measured using a conventional device (LIC), and, using this measurement as a regulating variable, the necessary amount of kettle feedwater, under a pressure of 2.5 MPa, is fed as coolant to the heat exchanger (34). 210 dm$^3$ of the kettle feedwater are necessary for the cooling, the water warming from 80° C. to 150° C., and leaving the heat exchanger (34) through the pipe (36). The amount of energy recovered is 185.7 kJ/kg of vinyl chloride.

The 1,2-dichloroethane, cooled to about 185° C., is fed to the second container (35) via a pipe loop having uniformly distributed apertures (37), and, in the second container, mixes with the hotter 1,2-dichloroethane which has risen into the second container from the first container (40) through the pipes (38), part of this 1,2-dichloroethane evaporating. In the first container (40), liquid 1,2-dichloroethane is warmed to boiling through heat exchange with the hot gas containing the vinyl chloride leaving the cracking zone (41) of the cracking furnace (33 plus 41) through the pipe (48). The heat exchange is favored by the "natural circulation", described above in greater detail, of the 1,2-dichloroethane between the first container (40) and the second container (35) via the rising pipes (38) and downward-leading pipes (39). The liquid/gas mixture in the rising pipes (38) has a temperature of 270° C., and the liquid in the downward-leading pipes (39) has a temperature of 265° C. According to the equation given above, the amount of 1,2-dichloroethane circulating between the first and second containers is 13,344 kg/hour. 6.25 kg of fresh, liquid 1,2-dichloroethane are fed per hour into the second container (35) per 100 kg of the liquid 1,2-dichloroethane circulating per hour between the first container (40) and the second container (35). The 1,2-dichloroethane essentially evaporated in the rising pipes (38) and the second container (35) is fed, free of liquid or solid components, through the pipe (42) into the radiation zone (41) of the cracking furnace (33 plus 41) in which the gaseous 1,2-dichloroethane is heated to 533° C. using four rows of burners located one above the other. The lower and upper rows of burners are provided with the same amount of fuel.

During the superheating of the gas to 533° C., part of the 1,2-dichloroethane is cracked into vinyl chloride and hydrogen chloride. As already stated above, the hot cracking product gases are fed to the first container (40) through the pipe (48) and leave this container with a temperature of 275° C. The average cooling rate of the cracking product gases in the first container (40) is 46° C./sec., i.e. 1/11.6 of the input temperature (533° C.) per second. These cracking product gases are fed to a further cooling stage according to the prior art (not represented in FIG. 3) through the pipe (44), during which they partly condense. From the mixture produced by thermal cracking, hydrogen chloride is removed by known methods in a column (likewise not represented in FIG. 3) at a head temperature of −24° C. The pressure at the head of this column is adjusted so that the gaseous, evaporated 1,2-dichloroethane leaves the second container (35) with a temperature of 270° C. In this container, 804 kg of 1,2-dichloroethane evaporate per hour at a pressure of 3.7 MPa. 2,880 kg of 1,2-dichloroethane are evaporated per hour per square meter of the liquid surface, taken as resting, in the second container (35). 30 kg of liquid 1,2-dichloroethane are drawn off per hour from the lower part of the first container (40) and fed, via the pipe (45), to a column in which 1,2-dichloroethane is distilled off overhead (not represented in FIG. 3). This is 3.6 kg of 1,2-dichloroethane drawn off per hour from the first container (40) per 100 kg of 1,2-dichloroethane freshly fed into the second container (35) per hour. The average residence time of 1,2-dichloroethane in the first and second containers together is 47 minutes.

The burners in the cracking furnace are provided via the pipe (43), with 0.103 Nm$^3$ of fuel (methane) per kg of vinyl chloride produced. The hot exhaust gases, which leave the 1,2-dichloroethane prewarming zone at 710° C., are cooled to 150° C. through production of steam and hot water before entering the atmosphere. In the upper part of the convection zone (33) of the cracking furnace, cooler water supplied via the pipe (51) is warmed and fed partly to the kettle (50) through the pipe (46), and partly used elsewhere in the process through the pipe (52). The hot water from the kettle (50) is fed through the pipe (47) to the central part of the convection zone (33) of the cracking furnace and fed back to the kettle (50) through the pipe (49) after taking up heat from the rising exhaust gases. Steam produced in this kettle is withdrawn through the pipe (53) and used elsewhere in the vinyl chloride production process. 114 kg of high-pressure steam (2.1 MPa, 215° C.) are produced per hour and output through the pipe (53). The energy recovered from this process is 843.9 kJ/kg of vinyl chloride. 201 dm$^3$ of hot water at 150° C. per hour are output through the pipe (52), and the amount of energy recovered during this process is 178.8 kJ/kg of vinyl chloride.

The conversion on cracking of 1,2-dichloroethane in the radiation zone (41) of the cracking furnace (33 plus 41) is 65%. 330 kg of vinyl chloride are produced per hour.

After a run time of 9 months, the heat transfer between the hot vinyl chloride-containing gases from the cracking furnace and the liquid 1,2-dichloroethane in the first container (40) is virtually unchanged. The temperature difference between the hot gases from the cracking furnace, which are drawn off from the first container (40) through the pipe (44), and the gaseous 1,2-dichloroethane leaving the second container (35) and being fed to the cracking furnace through the pipe (42) is 10° C. No noteworthy deposit is detected on the heat exchanger surfaces, neither on the side of the hot cracking product gases nor on the side of the liquid 1,2-dichloroethane. The energy recovered from the exhaust gases of the cracking furnace through production of hot water and high-pressure steam is 185.7+178.8+843.9=1,208.4 kJ/kg of vinyl chloride, corresponding to 0.034 Nm$^3$ of fuel (methane) per kg of vinyl chloride. The effective heating-gas consumption is thus reduced to 0.069 Nm$^3$/kg of vinyl chloride, i.e. only 67.4% of the amount (100%) arising from the comparison experiment. Accordingly, the energy saving is 32.6%, besides an increase in cracking conversion from 55 to 65% and a prolonging of the run time of the cracking furnace from 6 to 9 months.

EXAMPLE 2

Figure 4:
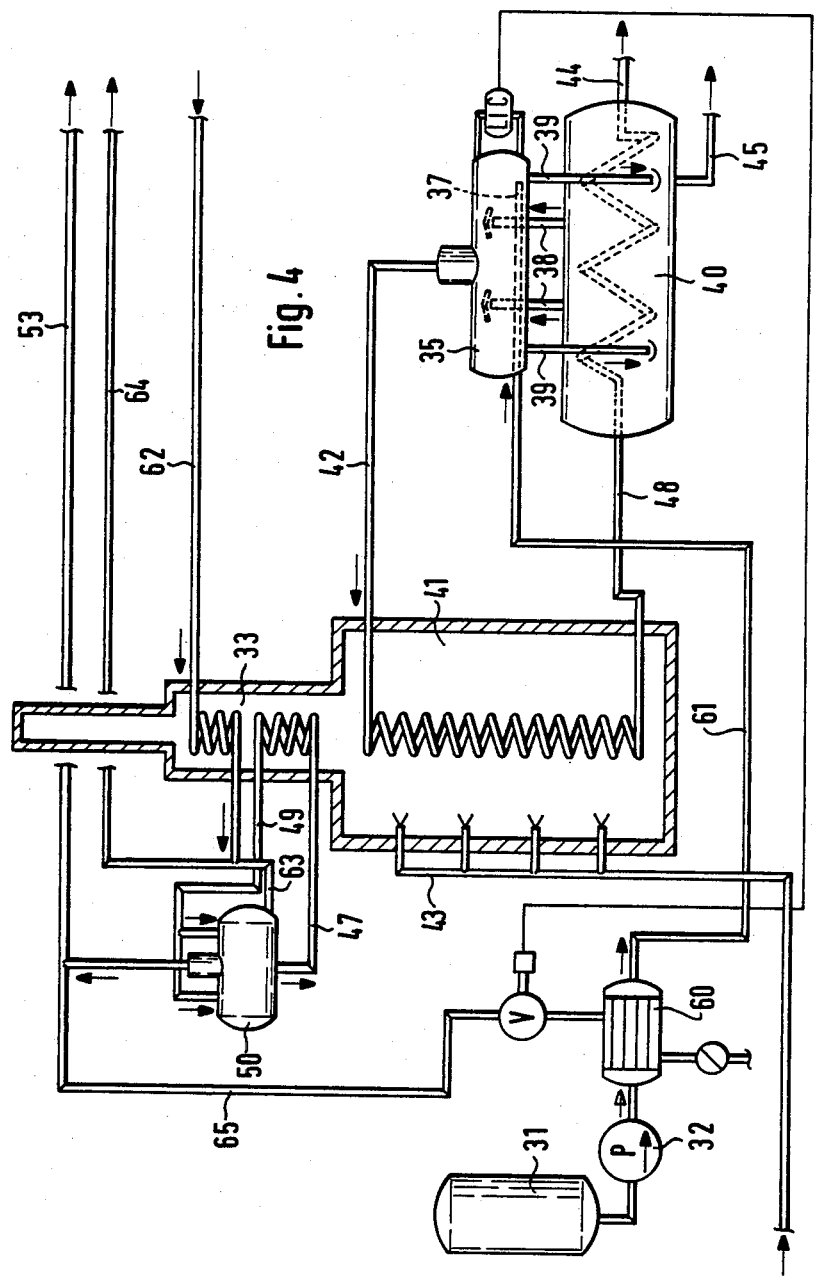

A procedure is followed according to the flowchart represented in FIG. 4. The apparatus parts labeled in this chart with the same numbers as in FIG. 3 have already been described in Example 1. The procedure in Example 2 differs from that in Example 1 merely in the following respects:

From a pump reservoir (31), 834 kg of 1,2-dichloroethane having a temperature of 130° C. are drawn off per hour and transported by means of the pump (32), under a pressure of 2.9 MPa and a temperature of 125° C., directly into the second container (35) via the heat exchanger (60) and via the pipe (61), but without warming in the convection zone (33) of the cracking furnace (33 plus 41). The heat exchanger (60) is heated with 25 kg of high-pressure steam (2.1 MPa pressure; 215° C.) per hour from the kettle (50) through the pipe (65). The feed of high-pressure steam to the heat exchanger (60) is regulated through measurement of the level of liquid 1,2-dichloroethane (LIC) in the second container (35) as the regulating variable. The 1,2-dichloroethane leaves the heat exchanger (60) with a temperature of 161° C. The hot, vinyl chloride-containing cracking product gases leave the radiation zone (41) of the cracking furnace (33 plus 41) through the pipe (48) with a temperature of 533° C., pass through the first container (40) and leave the latter with a temperature of 245° C. The cooling rate of the hot cracking product gases in the first container (40) is 51.7° C./sec., i.e. 1/10.3 of the input temperature (533° C.) into this container per second. After leaving the first container, the cracking product gases are cooled further by conventional methods, and hydrogen chloride is distilled off in a column having a head temperature of −31° C. The pressure at the head of this column is adjusted so that 1,2-dichloroethane leaves the second container (35) at a pressure of 2.6 MPa and a temperature of 240° C. 804 kg of 1,2-dichloroethane avaporate per hour in this container and in the rising pipes (38) and are fed to the radiation zone (41) of the cracking furnace through the pipe (42).

The temperature in the rising pipes (38) is 240° C., and that in the downward-leading pipes (39) is 235° C. From the equation described above, the amount of liquid 1,2-dichloroethane circulating between the first container (40) and the second container (35) works out at 13,177 kg/hour. 6.33 kg of fresh 1,2-dichloroethane are fed per hour into the second container (35) per 100 kg of 1,2-dichloroethane circulating per hour between the first and second containers. 30 kg of liquid 1,2-dichloroethane are drawn off per hour from the base of the first container (40) through the pipe (25) and fed to a column in which 1,2-dichloroethane is distilled off overhead, i.e. 3.6 kg/hour per 100 kg of 1,2-dichloroethane fed per hour into the second container (35). The average residence time of the 1,2-dichloroethane in the first and second containers together is 47 minutes, and 2,880 kg of 1,2-dichloroethane are evaporated per hour per m$^2$ of the liquid surface area taken as resting in the second container (35).

The four rows of burners arranged one above the other in the cracking furnace (33 plus 41) are supplied, via the pipe (43), with a total of 0.1074 Nm$^3$ of fuel (methane) per kilogram of vinyl chloride produced. In the upper part of the convection zone (33) of the cracking furnace (33 plus 41), 330 dm³ of kettle feed water (pressure 2.5 MPa), which is supplied via the pipe (62) at 80° C., are warmed to 150° C. in an economizer and is fed partly into the kettle (50) through the pipe (63) and is partly reused elsewhere in the vinyl chloride production process through the pipe (64). As in Example 1, the liquid from the kettle (50) is warmed in the lower part of the convection zone (33) and fed to the kettle (50) through the pipe (49).

As already stated above, part of the steam produced in the kettle (50) is used for heating the heat exchanger (60). The major part of this steam, namely 167 kg/hour, is utilized elsewhere in the process for the production of vinyl chloride.

Through this, 1,236.2 kJ of energy are recovered per kg of vinyl chloride. 136 dm³ of kettle feedwater at a temperature of 150° C. are fed per hour for further use through the pipe (64), through which 121 kJ of energy are recovered per kg of vinyl chloride. The total amount of energy recovered is 1,236.2+121=1,357.2 kJ/kg of vinyl chloride, corresponding to 0.038 Nm³ of fuel (methane) per kg of vinyl chloride. The effective heating-gas consumption is thus reduced to 0.0694 Nm³/kg, i.e. only 67.8% of the consumption (100%) which was necessary in the comparison experiment. Accordingly, the energy saving is 32.2%. As in Example 1, no noteworthy deposits are detected on the heat exchanger surfaces in the first container (40) after a run time of 9 months, and the cracking furnace run time is likewise at least 9 months. 330 kg of vinyl chloride are produced per hour, and the conversion for the cracking of 1,2-dichloroethane is 65%.

EXAMPLE 3

Figure 5:
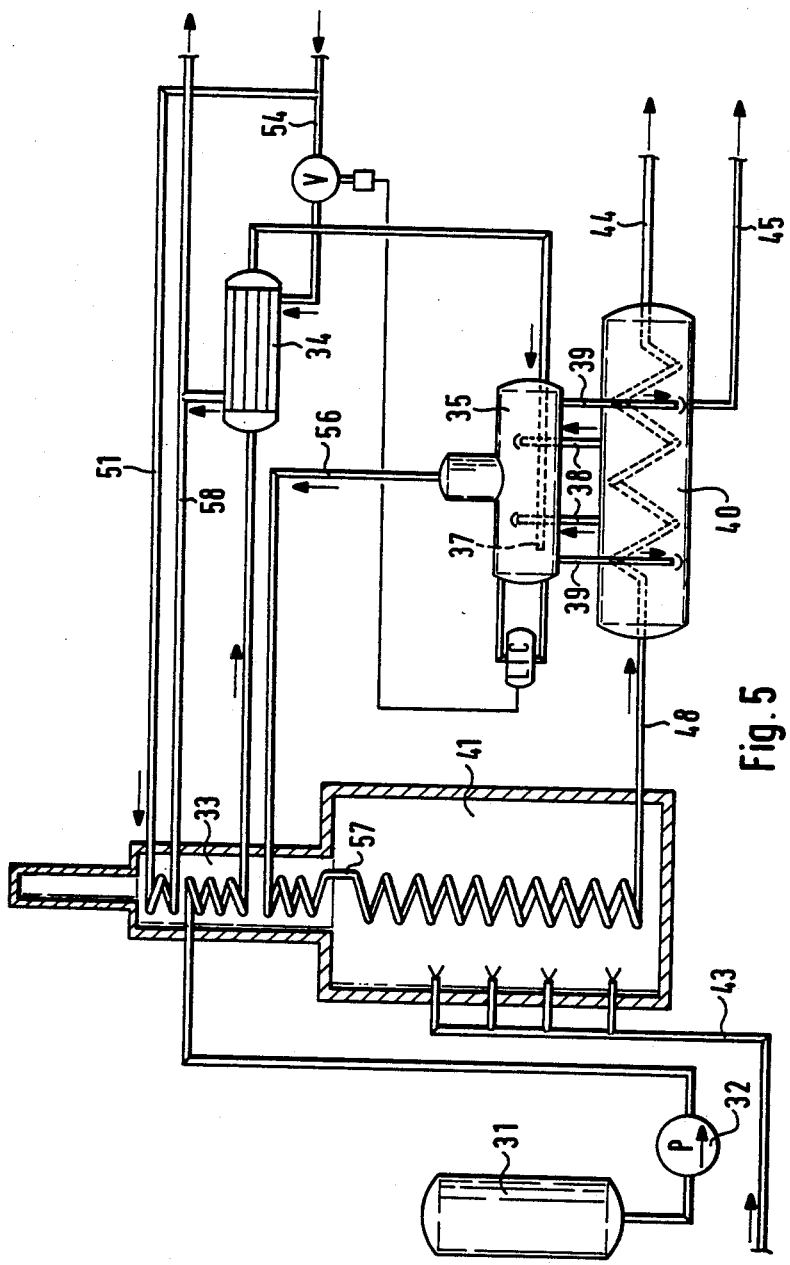

A procedure ia followed using the flowchart represented in FIG. 5. From a pump reservoir (31), 785 kg of 1,2-dichloroethane having a temperature of 130° C. are drawn off per hour and transported by means of the pump (32), under a pressure of 3.6 MPa and a temperature of 125° C., into the central region of the convection zone (33) of the cracking furnace (33 plus 41). The liquid 1,2-di-chloroethane is warmed to 210° C. by the exhaust gases drawn off from the radiation zone (41) of the cracking furnace. The energy equalization between the region (33) providing energy for the liquid 1,2-dichloroethane and the take-up of energy in the first container (40) required for evaporation of the 1,2-dichloroethane takes place in the heat exchanger (34). For this purpose, the level of the liquid 1,2-dichloroethane in the second container (35) is measured using a conventional device (LIC), and, using this measurement as the regulating variable, the necessary amount of kettle feedwater, under a pressure of 2.5 MPa, is fed as coolant to the heat exchanger (34) through the pipe (54). 180 dm³ of kettle feedwater are necessary for the cooling, the water being warmed from 100° C. to 130° C. and leaving the heat exchanger (34) through the pipe (55). The amount of energy recovered is 73.5 kJ/kg of vinyl chloride.

The 1,2-dichloroethane, cooled to about pipe (54). 195° C., is fed to the second container (35) through a pipe loop having uniformly distributed apertures (37), and, in this container, mixes with the hotter 1,2-dichloroethane which has risen into the second container from the first container (40) through the pipes (38), part of this 1,2-dichloroethane evaporating. The evaporated 1,2-dichloroethane at 262° C. and free of liquid or solid components, is introduced into the lower part of the convection zone (33) of the cracking furnace through the pipe (56) and is superheated there to about 400° C. From here, it is passed in to the radiation zone (41) through the pipe (57) and heated to 525° C.

During the superheating of the gas to 525° C., part of the 1,2-dichloroethane is cracked into vinyl chloride and hydrogen chloride. As described above, the hot cracking product gases are fed to the first container (40) through the pipe (48) and leave this container with a temperature of 268° C. The average cooling rate of the cracking product gases in the first container (40) is 41.5° C./sec., i.e. 1/12.6 of the input temperature (525° C.) per second. These cracking product gases are fed to a further cooling stage according to the prior art (not represented in FIG. 3) through the pipe (44), during which they partly condense. From the mixture produced by thermal cracking, hydrogen chloride is removed by a known method in a column (likewise not represented in FIG. 3) at a head temperature of −24° C. The pressure at the head of this column is adjusted so that the gaseous, evaporated 1,2-dichloroethane leaves the second container (35) with a temperature of 262° C. In this container, 776 kg of 1,2-dichloroethane evaporate per hour at a pressure of 3.5 MPa. 2,780 kg of 1,2-dichloroethane evaporate per hour per square meter of the liquid surface area taken as resting, in the second container (35). 24 kg of liquid 1,2-dichloroethane are drawn off per hour from the lower part of the first container (40) and fed through the pipe (45) to a column in which 1,2-dichloroethane is distilled off overhead (not represented in FIG. 3). This is 3.0 kg of 1,2-dichloroethane drawn off per hour from the first container (40) per 100 kg of 1,2-dichloroethane freshly fed to the second container (35) per hour. The average residence time of the 1,2-dichloroethane in the first and second containers together is 48 minutes.

The burners in the cracking furnace are supplied through the pipe (43) with 0.071 Nm³ of fuel (methane) per kilogram of vinyl chloride produced. In the upper part of the convection zone (33) of the cracking furnace, 110 kg of kettle feedwater at 100° C. are fed per hour through the pipe (51) and warmed to 130° C. The energy recovered in this process is 45.5 kJ/kg of vinyl chloride. 290 dm³ of hot water at 130° C. are output per hour through the pipe (58), the amount of energy recovered during this process being 119 kJ/kg of vinyl chloride.

The conversion during cracking of 1,2-dichloroethane in the radiation zone (41) of the cracking furnace (33 plus 41) is 65%. 312 kg of vinyl chloride are produced per hour.

After a run time of 9 months, the heat transfer between the hot, vinyl chloride-containing gases from the cracking furnace and the liquid 1,2-dichloroethane in the first container (40) is virtually unchanged. The temperature difference between the hot gases from the cracking furnace, which are drawn off from the first container (40) through the pipe (44), and the gaseous 1,2-dichloroethane leaving the second container (35) and being supplied to the cracking furnace through the pipe (56) is 10° C. No noteworthy deposit is detected on the heat exchanger surfaces, neither on the side of the hot cracking product gases nor on the side of the liquid 1,2-dichloroethane.

The energy recovered from the exhaust gases of the cracking furnace through production of hot water is 119 kJ/kg of vinyl chloride, corresponding to 0.003

Nm³ of fuel (methane) per kg of vinyl chloride. The effective heating gas consumption is thus reduced to 0.068 Nm³ per kg of vinyl chloride, i.e. only 66.4% of the amount (100%) arising from the comparison experiment. Accordingly, the energy saving is 33.6%, besides an increase in the cracking conversion from 55 to 65% and an extension of the run time of the cracking furnace from 6 to 9 months.

We claim:

1. A process for the production of vinyl chloride through thermal elimination of hydrogen chloride from 1,2-dichloroethane in a cracking furnace, liquid 1,2-dichloroethane being warmed indirectly and evaporated using the hot, vinyl chloride-containing gas leaving the cracking furnace, and the gaseous 1,2-dichloroethane being introduced to the cracking furnace, which comprises warming the 1,2-dichloroethane to boiling in a first container with the vinyl chloride-containing gas and transferring said 1,2-dichloroethane from here into a second container in which it is partially evaporated, without further warming, under a lower pressure than in the first container, the evaporated 1,2-dichloroethane being fed into the cracking furnace and the nonevaporated 1,2-dichloroethane being fed back to the first container.

2. The process as claimed in claim 1, wherein fresh, liquid 1,2-dichloroethane whose temperature is adjusted using temperature-control agents through the level of the liquid in the second container as the regulating variable, is fed into the second container.

3. The process as claimed in claim 1, wherein 1,000 to 10,000 kg of 1,2-dichloroethane are evaporated per hour per square meter of the surface area of the liquid, taken as resting, in the second container.

4. The process as claimed in claim 1, wherein fresh, liquid 1,2-dichloroethane having a temperature of 150° to 220° C. is introduced into the second container, this temperature being selected so that it is at least 20° C. below the temperature at which the 1,2-dichloroethane in gas form leaves the second container.

5. The process as claimed in claim 1, wherein 2 to 20 kg of fresh 1,2-dichloroethane are fed per hour into the second container per 100 kg of 1,2-dichloroethane circulating per hour between the first and second containers.

6. The process as claimed in claim 1, wherein 0.5 to 7 kg of liquid 1,2-dichloroethane are drawn off per hour from the first container, separated from solid components if necessary, and fed to a distillation column per 100 kg of liquid 1,2-dichloroethane freshly fed per hour into the second container.

7. The process as claimed in claim 1, wherein the average residence time of the 1,2-dichloroethane in the first and second containers together is 15 to 90 minutes.

8. The process as claimed in claim 1, the vinyl chloridecontaining gas leaving the first container after the indirect heat exchange being fed to a column for the removal of hydrogen chloride, the head temperature of the column being −20° to −50° C., wherein the pressure at the head of this column is adjusted so that the evaporated 1,2-dichloroethane leaves the second container with a temperature of 170° to 280° C.

9. The process as claimed in claim 1, wherein the fresh, liquid 1,2-dichloroethane, before it is fed into the second container, is warmed, either in the convection zone of the cracking furnace using the exhaust gas or using a temperature-control medium which has itself been warmed in the convection zone of the cracking furnace using the exhaust gas.

10. The process as claimed in claim 1, wherein the hot, vinyl chloride-containing gas leaving the cracking furnace is cooled, during the indirect warming of the 1,2-dichloroethane in the first container, at an average cooling rate per second of at least 1/15 of the temperature, in ° C., with which this gas enters the indirect warming zone of the 1,2-dichloroethane, until a temperature which is at least 5° C. above the evaporation temperature of the 1,2-dichloroethane in the second container is reached.

* * * * *